United States Patent [19]

Paszthory et al.

[11] 4,316,993

[45] Feb. 23, 1982

[54] PROCESS FOR THE PREPARATION OF 4-PHENOXY-PHENOLS

[75] Inventors: Emmerich Paszthory, Hofheim am Taunus; Karl G. Seifert, Frankfurt am Main; Vincenz Zimmermann, Nauheim; Hans J. Nestler, Kelkheim, all of Fed. Rep. of Germany

[73] Assignee: Hoechst Aktiengesellschaft, Frankfurt am Main, Fed. Rep. of Germany

[21] Appl. No.: 125,443

[22] Filed: Feb. 28, 1980

Related U.S. Application Data

[63] Continuation of Ser. No. 845,431, Oct. 25, 1977, abandoned.

[30] Foreign Application Priority Data

Oct. 27, 1976 [DE] Fed. Rep. of Germany ....... 2648644

[51] Int. Cl.$^3$ ............................................... C07C 41/26
[52] U.S. Cl. .................................... 568/637; 568/638; 568/633
[58] Field of Search ...................... 568/637, 638, 633

[56] References Cited

U.S. PATENT DOCUMENTS

| | | |
|---|---|---|
| 2,565,300 | 8/1951 | Faith et al. |
| 3,423,391 | 1/1969 | Kindler et al. .................. 260/141 |
| 3,914,325 | 10/1975 | Gavin et al. ..................... 568/775 |
| 3,998,642 | 12/1976 | Lau et al. ......................... 430/553 |

FOREIGN PATENT DOCUMENTS 735967  6/1966  Canada .............................. 568/637

OTHER PUBLICATIONS

Mahoney et al., WADC Technical Report, Sep. 1959, 59-173, p. 43.
Ullmanns Encyklopadie der Technischen Chemie, vol. 5, (1954), 812-813.
Gilman, Organic Synthesis Coll., vol. I, (1932), pp. 396-397.
Grillot et al., J.A.C.S., vol. 67, (1945), 1968-1969.
Weygand/Hilgetag, Preparative Organic Chemistry, (1972), pp. 343-344.
Adams et al., I. G. Farbenindustrie BIOS Final Report 1149, at 75-77.
Ullmanns Encyklopadie, 4th Edition, vol. 10, pp. 126-127.

*Primary Examiner*—Bernard Helfin
*Attorney, Agent, or Firm*—Curtis, Morris & Safford

[57] ABSTRACT

Diazotization of 4-phenoxy-anilines in aqueous sulfuric acid of 60 to 75% strength and decomposition of the resulting diazonium compound in sulfuric acid of the same concentration range yields the corresponding phenols in high yields and quality. These phenols are intermediate for the corresponding 4-phenoxy-phenoxy alkane carboxylic acids which are pharmaceuticals capable of reducing the blood serum lipid level.

16 Claims, No Drawings

PROCESS FOR THE PREPARATION OF 4-PHENOXY-PHENOLS

This is a continuation of application Ser. No. 845,431, filed Oct. 25, 1977, and now abandoned.

The present invention relates to a process for the preparation of 4-phenoxy-phenols.

In German Offenlegungsschrift No. 21 36 828, a process has been described for the preparation of compounds of the formula I

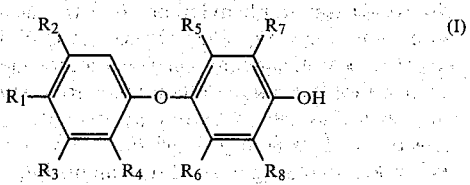

in which $R_1$ stands for hydrogen, methylthio, cyclopentyl, cyclohexyl, phenyl, methylcyclohexyl or ethylcyclohexyl or halogen, preferably chlorine, $R_2$ and $R_3$ represent, independent of each other, hydrogen, halogen, preferably chlorine, or alkyl having 1 to 4 carbon atoms, $R_4$ is hydrogen, alkyl having 1 to 4 carbon atoms, cyclopentyl, cyclohexyl, halogen, preferably chlorine, or $R_3$ and $R_4$ together may form a —CH=CH—CH=CH—bridge, and $R_5$, $R_6$, $R_7$ and $R_8$ represent, independent of each other, hydrogen or alkyl having 1 to 4 carbon atoms.

In this process an aniline of the formula II

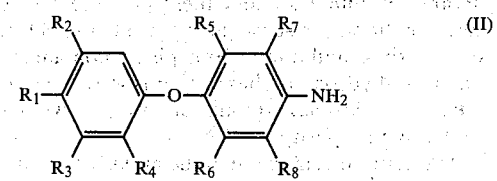

in which the radicals $R_1$ through $R_8$ are defined as above, is diazotized with nitrous acid and is reacted with hydrofluoboric acid to give the sparingly soluble salt of the formula III

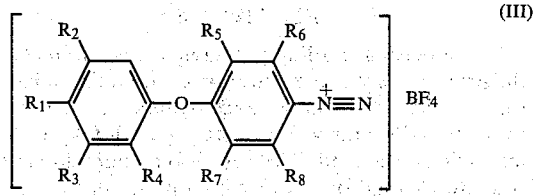

in which the radicals $R_1$ to $R_8$ are defined as above. This salt is reacted in boiling acetic anhydride to give the corresponding acetoxyphenol which is converted into the free phenol of the formula I by splitting off the acetyl group with an alkali. For the diazotization, the aniline is in this case dissolved in glacial acetic acid, and the hydrochloride is precipitated with hydrochloric acid.

In the above-mentioned German Offenlegungsschrift it has also been described how to convert these 4-phenoxy-phenols into 4-phenoxy-phenoxyalkane-carboxylic acids and the salts thereof which influence the blood serum lipid level. It has also been described therein how to obtain the starting materials.

It has now been found that the preparation of the phenol from the above-mentioned aniline can be considerably simplified and can also be carried out on an industrial scale, without using glacial acetic acid, hydrofluoboric acid and acetanhydride and without having to face a reduction of quality or yield.

Thus, the present invention provides an improved process for the preparation of the compounds of the formula I by diazotizing the anilines of the formula II and decomposing the diazonium compounds, which comprises diazotizing the anilines of the formula II in 60 to 75% sulfuric acid and decomposing them directly in a sulfuric acid of equal concentration.

In the following, some preferred embodiments of the invention are described in detail.

Preferred starting materials are the halogenated 4-phenoxy-anilines, especially the chlorine derivatives. Particularly preferred are 2,4-dichloro- and 4-chloro-4'-aminodiphenyl-ether.

The sulfuric acid concentration is preferably about 65%. The diazotization of the aniline of the formula II may be effected in a sulfuric acid-aniline sulfate suspension with a higher sulfuric acid concentration, so that upon completion of the diazotization with anhydrous sodium nitrite the sulfuric acid concentration is about 65%, which is also an optimum value for the decomposition step.

The diazotization is effected in a particularly rapid manner in the presence of alkali metal chlorides under adiabatic conditions.

As alkali metal chlorides there may be mentioned potassium chloride and especially sodium chloride.

For the decomposition step it is recommended to add a water-immiscible solvent to the phenol, in order to extract the product from the aqueous medium and thus to avoid side reactions. As solvents of this kind there are mentioned especially toluene and xylene.

For carrying out the process on an industrial scale it is advantageous to introduce the diazonium sulfate solution in sulfuric acid into a pre-charged mixture of sulfuric acid of about 65% strength and xylene which has been preheated to a temperature in the range of from 115° to 130° C., preferably from 120° to 125° C. Under these conditions a rapid and controlled decomposition (exchange of the diazonium group for the phenolic hydroxy group) is effected.

The nitrogen set free in the decomposition step is saturated with the solvent vapor. The recovery of this evaporated solvent requires energy, as does the evaporation. Surprisingly, it has now been found that it is possible to carry out this reaction of splitting off gas without a reduction in yield under excess pressure, preferably in the range of from 1 to 1.5 bars. By this increase in pressure, the partial pressure of the solvent in the nitrogen split off is considerably reduced.

The energy requirement in the reaction vessel may also be reduced by preheating the solution of the diazonium salt being introduced up to about 105° C., preferably to a temperature of from 60° to 80° C.

The sulfuric acid remaining in the decomposition reaction mixture may be recycled several times into the process, after being concentrated accordingly and following the separation of water and alkali metal hydrogensulfate, if necessary.

The process of the invention is effected in an unobjectionable manner from the ecological point of view and is extremely economical due to the favorable energy utilization.

The following Examples serve to illustrate the invention, the percentages being percent by weight.

EXAMPLE 1

1,250 Grams of 65% sulfuric acid are heated to 70° C. in a 1 liter glass flask. Afterwards 120 g of 2,4-dichloro-4'-amino-diphenylether are introduced, and the mixture is stirred for 30 minutes at 110° C. Subsequently the mixture is cooled to 35° C., 6 g of sodium chloride are added, and then 38.4 g of solid sodium nitrite are introduced within one hour. The diazotization is completed after 3 hours, whereupon insoluble impurities are separated from the diazonium salt solution.

300 Grams of 65% sulfuric acid and 414 g of xylene are placed into a 2 liter glass flask. The diazonium salt solution is added within 50 minutes, while stirring, at a temperature of from 115° to 123° C. below the surface of the sulfuric acid-xylene mixture. In the course of this process 7.5 l of nitrogen escape. The reaction mixture is then continued to be stirred vigorously for one hour at a temperature in the range of from 120° to 123° C. In the course of this process, another 4.4 l of nitrogen escape. The reaction mixture is then allowed to cool, while stirring, and the xylene phase is separated. By way of a quantitative gas chromatographic analysis a content of 20.7% of 2,4-dichloro-4'-hydroxy-diphenylether is determined, which corresponds to a yield of 90%.

EXAMPLE 2

2,500 kg of 65% sulfuric acid are placed into a 2 m³ steel-enamel kettle and are heated while stirring to 70° C. Thereafter 240 kg of 2,4-dichloro-4'-amino-diphenylether are introduced, the mixture is continued to be stirred for 30 minutes at 110° C. and is subsequently cooled to 35° C. and pressed into a 3 m³ steel-enamel vessel, into which 2 kg of sodium chloride and—within 2 hours—70 kg of solid sodium nitrite are added continuously via a feed screw.

In the meantime a 4 m³ steel-enamel vessel is charged with 470 kg of 65% sulfuric acid and 864 kg of xylene, which mixture is heated to a temperature in the range of from 120° to 123° C. Upon completion of the diazotization the diazonium salt solution is preheated via a heat exchanger to 60° to 65° C. and is pressed within 45 minutes under the surface of the sulfuric acid-xylene mixture. During the decomposition process, a temperature in the range of from 120° to 122° C. is maintained. After 1 hour the gas development is completed, whereupon the temperature of from 120° to 122° C. is maintained for yet another hour and is then reduced to 40° C. The xylene phase is separated. A quantitative gas chromatographic analysis shows a content of 19.7% of 2,4-dichloro-4'-hydroxy-diphenylether, which corresponds to a yield of 89%.

EXAMPLE 3

The process according to Example 2 is repeated with the proviso that in the decomposition process an excess pressure of 1.5 bars is maintained. During the decomposition step the vessel needs no longer to be heated with 4 bars, but only with from 1.2 to 1.5 bars of steam over-pressure. The quality and yield have not been altered in any manner.

EXAMPLE 4

2,400 kg of 61% sulfuric acid obtained from the process according to Example 2 are concentrated with 280 kg of 95% sulfuric acid to a strength of 65% and are used once again. The quality and yield of the product have not been altered in any manner.

EXAMPLE 5

2,400 kg (1,650 l) of 65% sulfuric acid are placed into a 2 m³ steel-enamel vessel with stirrer. 258 kg of 4-chloro-4'-amino-diphenylether are introduced portion-wise, while stirring. Then the vessel is closed and is heated to 106° C. under an inert gas atmosphere. At this temperature the mixture is continued to be stirred for 30 minutes and is subsequently cooled to 35° C. The suspension is filled into a 3 m³ steel-enamel vessel, and within 4 hours 93 kg of solid sodium nitrite are continuously added via a feed screw. The stirring speed is 54 rpm during the first 2 hours of the diazotization and subsequently 30 rpm; the temperature rises from 32° C. at the start to 42° C.

In the meantime, 477 kg of 65% sulfuric acid are placed into a 4 m³ enamel vessel with stirrer, which then is charged with 867 kg (1,000 l) of xylene and preheated to 122° C.

Upon completion of the diazotization, the diazonium sulfate solution is preheated via a preheater to 70° C. and is evenly added within one hour under the surface of the preheated sulfuric acid-xylene mixture. During the decomposition reaction, a temperature in the range of from 122° to 125° C. is maintained, the over-pressure being 1.0 bar. The mixture is continued to be stirred for another 30 minutes under these pressure and temperature conditions, is subsequently cooled to 80° C. without stirring, and the xylene phase containing the 4-chloro-4'-hydroxy-diphenylether is separated. A quantitative gas chromatographic analysis shows a yield of 91.3% with a purity of 95.6%.

The sulfuric acid phase of the mixture is cooled to 10° C. and the sodium hydrogensulfate formed (with 1 mole of crystal water) is eliminated. The sulfuric acid is concentrated with 280 kg of 96% sulfuric acid to its original strength of 65% and is recycled into the process. In the following reactions the yield and quality of the product are not altered in any manner.

EXAMPLE 6

The process according to Example 2 is repeated with the proviso that the diazotization of the amine sulfate of the 2,4-dichloro-4'-amino-diphenylether suspended in the 65% sulfuric acid is effected with 305 kg of 40% nitrosyl-sulfuric acid. The gas chromatographic analysis shows a yield of 92.6% with a purity of 97.2%.

What is claimed is:

1. In a process for the preparation of a phenol of the formula

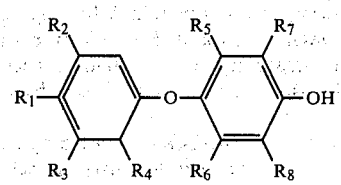

in which $R_1$ is hydrogen, halogen, methylthio, cyclopentyl, cyclohexyl, methylcyclohexyl, ethylcyclohexyl or phenyl, $R_2$ and $R_3$, which are the same or different, each is hydrogen, halogen or alkyl of from 1 to 4 carbon atoms, $R_4$ is hydrogen, halogen, alkyl of from 1 to 4 carbon atoms, cyclopentyl or cyclohexyl or $R_3$ and $R_4$ together are —CH=CH—CH=CH—, and $R_5$, $R_6$, $R_7$ and $R_8$, which are the same or not all the same, each is hydrogen or alkyl of from 1 to 4 carbon atoms, by diazotizing an aniline of the formula

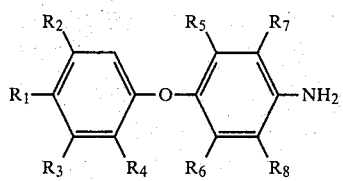

and decomposing the diazonium compound, the improvement which comprises diazotizing by introducing said aniline into aqueous sulfuric acid of a concentration of from 60 to 75% by weight and then adding sodium nitrite thereto; and decomposing diazonium compound which is a product of the diazotization by combining said compound with a preheated mixture, the temperature of which is maintained in the range of from 115° to 130° C., of aqueous sulfuric acid of substantially the same concentration as above and a water-immiscible solvent capable of dissolving said phenol.

2. A process as claimed in claim 1, wherein the concentration of the sulfuric acid is about 65% by weight.

3. A process as claimed in claim 1, wherein the diazotization reaction is performed under adiabatic conditions.

4. A process as claimed in claim 1 which further comprises diazotizing in the presence of an alkali metal chloride.

5. A process as claimed in claim 4, wherein the alkali metal chloride is potassium chloride or sodium chloride.

6. A process as claimed in claim 1, wherein the solvent is xylene.

7. A process as claimed in claim 1, wherein the temperature is 120° to 125° C.

8. A process as claimed in claim 1 which is performed at greater than atmospheric pressure.

9. A process as claimed in claim 8, wherein the pressure is 1 to 1.5 bar greater than atmospheric pressure.

10. A process as claimed in claim 1, wherein the sulfuric acid is isolated after the decomposition reaction, adjusted to its original concentration and recycled into the process.

11. A process as claimed in claim 1 wherein $R_1$, $R_2$, $R_3$ and $R_4$ are the same or not all the same and each is hydrogen or halogen and $R_5$, $R_6$, $R_7$ and $R_8$ are hydrogen.

12. A process as claimed in claim 11, wherein $R_1$, $R_2$, $R_3$ and $R_4$ are the same or not all the same and each is hydrogen or chlorine.

13. A process as claimed in claim 1, wherein $R_1$ is halogen, $R_4$ is hydrogen or halogen and $R_2$, $R_3$, $R_5$, $R_6$, $R_7$ and $R_8$ are hydrogen.

14. A process as claimed in claim 13, wherein the solution of the diazonium compound is preheated before it is added to the mixture of sulfuric acid and solvent.

15. A process as defined in claim 1, wherein subsequent to diazotization insoluble impurities are separated from the diazotization reaction mixture to form a diazonium salt solution and, then, said solution is added to the mixture of sulfuric acid and solvent.

16. In a process for the preparation of a phenol of the formula

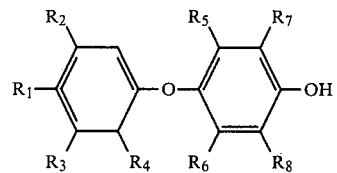

in which $R_1$ is hydrogen, halogen, methylthio, cyclopenyl, cyclohexyl, methylcyclohexyl, ethylcyclohexyl or phenyl, $R_2$ and $R_3$, which are the same or different, each is hydrogen, halogen or alkyl of from 1 to 4 carbon atoms, $R_4$ is hydrogen, halogen, alkyl of from 1 to 4 carbon atoms, cyclopentyl or cyclohexyl or $R_3$ and $R_4$ together are —CH=CH—CH=CH—, and $R_5$, $R_6$, $R_7$ and $R_8$, which are the same or not all the same, each is hydrogen or alkyl of from 1 to 4 carbon atoms, by diazotizing an aniline of the formula

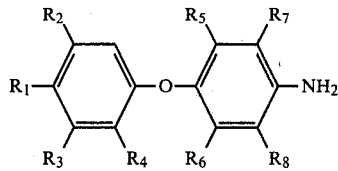

and decomposing the diazonium compound, the improvement which comprises diazotizing by introducing said aniline into aqueous sulfuric acid of a concentration of from 60 to 75% by weight and then adding solid sodium nitrite thereto; decomposing the diazonium compound which is a product of the diazotization by combining said compound with a preheated mixture, the temperature of which is maintained in the range of from 115° to 130° C., of aqueous sulfuric acid of substantially the same concentration as above and a water-immiscible solvent capable of dissolving said phenol; and after decomposition isolating sulfuric acid from the decomposition mixture, adjusting the sulfuric acid to its original concentration and recycling same to the diazotization.

* * * * *